United States Patent
Besson et al.

(10) Patent No.: US 12,357,273 B2
(45) Date of Patent: Jul. 15, 2025

(54) APPARATUS AND METHOD FOR ESTIMATING A VELOCITY OF AT LEAST ONE SCATTERER IN A MEDIUM

(71) Applicant: E-SCOPICS, Aix-en-Provence (FR)

(72) Inventors: Adrien Besson, Marseilles (FR); Frederic Wintzenrieth, Aix-en-Provence (FR)

(73) Assignee: E-SCOPICS, Aix-en-Provence (FR)

( * ) Notice: Subject to any disclaimer, the term of this patent is extended or adjusted under 35 U.S.C. 154(b) by 83 days.

(21) Appl. No.: 18/042,747

(22) PCT Filed: Aug. 27, 2021

(86) PCT No.: PCT/EP2021/073794
§ 371 (c)(1),
(2) Date: Feb. 23, 2023

(87) PCT Pub. No.: WO2022/043524
PCT Pub. Date: Mar. 3, 2022

(65) Prior Publication Data
US 2023/0355209 A1    Nov. 9, 2023

Related U.S. Application Data

(60) Provisional application No. 63/071,044, filed on Aug. 27, 2020.

(51) Int. Cl.
*A61B 8/00* (2006.01)
*A61B 8/06* (2006.01)

(52) U.S. Cl.
CPC .............. *A61B 8/4494* (2013.01); *A61B 8/06* (2013.01); *A61B 8/488* (2013.01)

(58) Field of Classification Search
None
See application file for complete search history.

(56) References Cited

U.S. PATENT DOCUMENTS

2011/0051554 A1  3/2011  Varray et al.
2014/0257103 A1*  9/2014  Jensen ................ G01S 15/8984
                                               600/441

(Continued)

OTHER PUBLICATIONS

J. Jensen et al, "Convex Array Vector Velocity Imaging Using Transverse Oscillation and Its Optimization", IEEE Transactions on Ultrasonics, Ferroelectrics, and Frequency Control, vol. 62, No. 12, pp. 2043-2053, Dec. 2015 (Year: 2015).*

(Continued)

*Primary Examiner* — Joel Lamprecht
*Assistant Examiner* — Nyrobi Celestine
(74) *Attorney, Agent, or Firm* — WOMBLE BOND DICKINSON (US) LLP

(57) ABSTRACT

An apparatus for estimating a velocity of at least one scatterer in a medium, the apparatus including a curved array of virtual transducers ($T_1$-$T_n$) for emitting Archimedean spiral waves in a plurality of predetermined directions of propagation defined by a set of insonification angles, and for receiving, from the at least one scatterer, scattered signals generated by scattering of the Archimedean spiral waves emitted from the curved array of virtual transducers, a driving and processing unit ($U_c$) for estimating the velocity of the at least one scatterer.

14 Claims, 8 Drawing Sheets

(56) References Cited

U.S. PATENT DOCUMENTS

2018/0038955 A1* 2/2018 Jensen .............. G01S 15/8925
2019/0346564 A1 11/2019 Dzikowicz

OTHER PUBLICATIONS

Aki, K., et al., "Quantitative Seismology", Univ Science Books, 2002, 10 pages.

Angelsen, B. A. J., "Instantaneous Frequency, Mean Frequency, and Variance of Mean Frequency Estimators for Ultrasonic Blood Velocity Doppler Signals", IEEE Transactions on Biomedical Engineering, vol. BME-28, No. 11, Nov. 1981, pp. 733-741.

Bae, S., et al., "Ultrasonic sector imaging using plane wave synthetic focusing With a convex array transducer", J. Acoust. Soc. Am., vol. 144, No. 5, 2018, 19 pages.

Benech, N., et al., "Near-field effects in Green's function retrieval from cross-correlation of elastic fields: experimental study with application to elastography", The Journal of the Acoustical Society of Ameria, vol. 133, No. 5, May 6, 2013, pp. 2755-2766.

Bercoff, J., et al., "Supersonic shear imaging: a new technique for soft tissue elasticity mapping", IEEE Transactions on Ultrasonics, Ferroelectrics, and Frequency Control, vol. 51, No. 4, Apr. 2004, pp. 396-409.

Bercoff, J., et al., "The Role of Viscosity in the Impulse Diffraction Field of Elastic Waves Induced by the Acoustic Radiation Force", IEEE Trans. Ultrason. Ferroelectr. Freq. Control, vol. 51, No. 11, Dec. 2004, pp. 1523-1536.

Besson, A., et al., "On Archimedean-spiral-based Imaging", IEEE Int. Ultrason. Symp. IUS, Sep. 11, 2020, pp. 1-4.

Besson, A., et al., "Vector-flow Imaging in Convex-array Configurations", IEEE International Ultrasonics Symposium (IUS), 2020, 4 pages.

Bonnefous, O., et al., "Time domain formulation of pulse-Doppler ultrasound and blood velocity estimation by cross correlation", Ultrasonic Imaging, vol. 8, No. 2, Apr. 1986, pp. 73-85.

Catheline, S., et al., "Time Reversal of Elastic Waves in Soft Solids", Phys. Rev. Lett., vol. 100, Feb. 15, 2008, p. 064301.

Catheline, S., et al., "Tomography from diffuse waves: Passive shear wave imaging using low frame rate scanners", Applied Physics Letters, vol. 103, No. 1, Jul. 1, 2013, p. 014101.

Chen, D. C., et al., "Focused acoustic vortex by an artificial structure with two sets of discrete Archimedean spiral slits", Appl. Phys. Lett., vol. 115, No. 8, 2019, 6 pages.

Denarie, B., et al., "Coherent Plane Wave Compounding for Very High Frame Rate Ultrasonography of Rapidly Moving Targets", IEEE Transactions on Medical Imaging, vol. 32, No. 7., Jul. 7, 2013, pp. 1265-1276.

Dunmire, B., et al., "Cross-beam vector Doppler ultrasound for angle-independent velocity measurements", Ultrasound in Medicine & Biology, vol. 26, No. 8, Oct. 2000, pp. 1213-1235.

International Preliminary Report on Patentability received for PCT Patent Application No. PCT/EP2021/073794, mailed on Mar. 9, 2023, 9 pages.

International Search Report and Written Opinion received for PCT Patent Application No. PCT/EP2021/073794, mailed on Nov. 23, 2021, 11 pages.

Jensen, J. A., et al., "A New Method for Estimation of Velocity Vectors", IEEE Trans. Ultrason. Ferroelectr. Freq. Control, vol. 45, No. 3, May 1998, pp. 837-851.

Jensen, J. A., et al., "Ultrasound Vector Flow Imaging—Part I: Sequential Systems", IEEE Transactions on Ultrasonics, Ferroelectrics, and Frequency Control, vol. 63, No. 11, Nov. 2016, pp. 1704-1721.

Jensen, J. A., et al., "Ultrasound Vector Flow Imaging—Part II: Parallel Systems", IEEE Trans. Ultrason. Ferroelectr. Freq. Control, vol. 63, No. 11, Nov. 2016, pp. 1722-1732.

Jensen, J. A., et al., "A Model for the Propagation and Scattering of Ultrasound in Tissue", J. Acoust. Soc. Am., vol. 89, No. 1, 1991, pp. 182-190.

Kasai, C., et al., Real-Time Two-Dimensional Blood Flow Imaging Using an Autocorrelation Technique, IEEE Transactions on Sonics and Ultrasonics, vol. SU-32, No. 3, May 1985, 7 pages.

Liu, J., et al., "Archimedean spiral based compounding for high quality and high frame rate convex array imaging", in 2017 IEEE International Ultrasonics Symposium (IUS), Retrieved from: https://www.researchgate.net/publication/319177836, Sep. 2017, 2 pages.

Loupas, T., et al., "An axial velocity estimator for ultrasound blood flow imaging, based on a full evaluation of the Doppler equation by means of a two-dimensional autocorrelation approach", IEEE Transactions on Ultrasonics, Ferroelectrics, and Frequency Control, vol. 42, No. 4, Jul. 1995, pp. 672-688.

Montaldo, G., et al., "Coherent plane-wave compounding for very high frame rate ultrasonography and transient elastography", IEEE Transactions on Ultrasonics, Ferroelectrics and Frequency Control, vol. 56, No. 3., 2009, pp. 489-506.

Sanchez-Sesma, F. J., et al., "Diffuse fields in dynamic elasticity", Wave Motion, vol. 45, No. 5, Apr. 2008, pp. 641-654.

Stahli, P., et al.,"Improved forward model for quantitative pulse-echo speed-of-sound imaging", Ultrasonics, vol. 108, No. 106168, Dec. 2020, 17 pages.

Tanter, M., et al., "Ultrafast Compound Imaging for 2-D Motion Vector Estimation: Application to Transient Elastography", IEEE Trans. Ultrason. Ferroelectr. Freq. Control, vol. 49, No. 10, Oct. 2002, pp. 1363-1374.

Trahey, G. G., et al., "Angle Independent Ultrasonic Detection of Blood Flow", IEEE Trans. Biomed. Eng., vol. BME-34, No. 12, Aug. 14, 1987, pp. 965-967.

Yiu, B. Y. S., et al., "Vector Projectile Imaging: Time-Resolved Dynamic Visualization of Complex Flow Patterns", Ultrasound in Medicine & Biology, vol. 40, No. 9, Sep. 2014, pp. 2295-2309.

* cited by examiner (a) Cartesian space.

(b) Pseudo polar space.  (c) Polar space

APPARATUS AND METHOD FOR ESTIMATING A VELOCITY OF AT LEAST ONE SCATTERER IN A MEDIUM

FIELD OF THE INVENTION

The present invention relates to a method and an apparatus for estimating the velocity vector of at least one scatterer in a medium (a remotely sensed object or group of objects) using either sound (in particular ultrasound), or electro-magnetic radiation.

More particularly, the invention concerns a Vector Flow Imaging (VFI) method and apparatus which are valuable diagnostic tools that perform angle independent flow estimation and provide clinicians with axial and lateral velocity components.

The movement of the scatterer is determined by emitting and receiving a pulsed wave field with an array of transducers. By using a number of pulse emissions, the inter pulse movement can be estimated and the velocity found from the estimated movement and the time between pulses.

BACKGROUND OF THE INVENTION

Non-invasive visualization and measurements of flow dynamics using ultrasound (US) is considered to be of major clinical importance e.g. to highlight abnormal vascular conditions.

Standard techniques, e.g. color-flow imaging, continuous-wave Doppler and pulsed-wave Doppler, offer one dimensional views and measurements of the flow along the direction of the ultrasound beam. Such methods suffer from an intrinsic methodological flaw due to their dependency to the angle between the direction of the flow and the one of the US beam.

This may be problematic in cases where one may encounter tortuous vasculature, e.g. at carotid bifurcation. It also may lead to counter intuitive velocity fields in the case of polar field of views, e.g. convex probe geometries for abdominal clinical applications.

Vector Flow Imaging (VFI) methods solve this problem by providing both axial and lateral components of the velocity flow. Different techniques have been described in the literature such as multi-beam Doppler, inter-frame speckle tracking or transverse oscillation.

With the massive adoption of ultrafast US imaging in the community, multi-beam methods have drawn significant interest recently. Indeed, the idea is to benefit from both the high directivity and the unfocused aspect of plane waves to derive vector flow information from projections along the direction of the transmit beam at high frame rates, therefore reducing the potential for aliasing.

While VFI techniques have been extensively studied because of their capability of outlining detailed depiction and visual quantification of complex flow behavior in vascular systems of a patient, there is a need for a new VFI technique more suited to deep vascular imaging, e.g. portal vein imaging, where imaging is usually performed with curvilinear array of transducers.

An aim of the present invention is to provide an apparatus and a method suited to sectorial imaging.

SUMMARY OF THE INVENTION

For this purpose, the invention proposes an apparatus for estimating a velocity of at least one scatterer in a medium, the apparatus comprising:

a generator for generating excitation signals,
a curved array of virtual transducers for transforming said excitation signals into Archimedean spiral waves and for:
  emitting said Archimedean spiral waves in a plurality of predetermined directions of propagation defined by a set of insonification angles $\alpha_i$, a curvature of said curved array of virtual transducers defining a reference center O and a radius of curvature $r_n$), and
  receiving, from said at least one scatterer, scattered signals generated by scattering of said Archimedean spiral waves emitted from said curved array of virtual transducers,
a driving and processing unit for driving the generator and the curved array of virtual transducers, and for estimating the velocity of the at least one scatterer,
wherein axial and lateral velocity components (of the beam) are estimated using a set of local wavefront orientations $\alpha_{eq,i}$ of the Archimedean spiral waves as a function of the initial set of insonification angles $\alpha_i$, the geometry of the curved array of virtual transducers and the distance r to the reference center O, each local wavefront orientation satisfying the following formula:

$$\alpha_{eq,i} = \arcsin\left(\frac{r_n}{r}\sin\alpha_i\right).$$

In the context of the present invention, the term "virtual transducer array" is understood to mean a set of points defining a geometric shape chosen as a function of delay laws applied to the real array of transducers so that the said points of the set emit a spiral wavefront.

A virtual array of transducers is a set of points in the medium located along an arc. The characteristics of the spiral wavefront are chosen (in particular the initial emitting angle) in reference to this array of virtual transducers. The delay laws to apply to the real transducer array are derived subsequently. In the framework of the wavefront approximation, everything occurs as if the waves were emitted by the virtual array of transducers.

Preferred—but non-limiting—aspects of the apparatus according to the invention are the following:

the driving and processing unit can comprise a controller for driving the generator in order to generate at least two series of excitation signals at a constant repetition interval $T_P$, and for driving the curved array of virtual transducers for transforming said at least two series of excitation signals into Archimedean spiral waves:
  a first series of excitation signals allowing the obtaining of a first gathering of scattered signals, and
  a second series of excitation signals allowing the obtaining of a second gathering of scattered signals;
the driving and processing unit can further comprise a beamformer for:
  receiving said first and second gatherings of scattered signals generated by scattering of said Archimedean spiral waves, and for
  delaying and summing said first gathering of scattered signals in order to generate first groups of receive beams having a respective receive angle $\beta_j$, each group of receive beams corresponding to a respective insonification angle $\alpha_i$,
  delaying and summing said second gathering of scattered signals in order to generate second groups of receive beams having a respective receive angle $\beta_j$, each group of receive beams corresponding to a respective insonification angle $\alpha_i$;

each of the first and second groups of receive beams can comprise a plurality of images, each image being associated with a respective pair of insonification angle $\alpha_i$ and receive angle $\beta_j$, the driving and processing unit further comprising a processor for Doppler processing said first and second groups of receive beams for any given pair of images of the first and second groups of receive beams having the same pair of insonification angle $\alpha_i$ and receive angle $\beta_j$ so that velocity fields are estimated for each pair of distinct spiral orientations and receive beam orientations;

the processor can be configured for implementing the following steps for each pair of images of the first and second groups of receive beams having the same pair of insonification angle $\alpha_i$ and receive angle $\beta_j$:

estimating a displacement field for each corresponding pixel between the images of a given pair of images, estimating, from the displacement field, a doppler frequency shift per pixel for said given pair of images;

the processor can be adapted for implementing an algebraic inversion step where several projections of the velocity field and their known orientations are used to estimate radial and azimuthal components of the velocity field;

the processor can be adapted for estimating axial and lateral velocity components from the radial and azimuthal components of the velocity field.

The invention further concerns a method for estimating the velocity of at least one scatterer in a medium, the method comprising:

generating excitation signals, transforming said excitation signals into Archimedean spiral waves, emitting said Archimedean spiral waves in a plurality of predetermined directions of propagation defined by a set of insonification angles ($\alpha_i$), a curvature of said curved array of virtual transducers defining a reference center (O) and a radius of curvature ($r_n$), receiving scattered signals generated by scattering of said Archimedean spiral waves emitted from said curved array of virtual transducers, estimating the velocity of the at least one scatterer, wherein (during the estimating step) axial and lateral velocity components (of the beam) are estimated using a set of local wavefront orientations ($\alpha_{eq,i}$) of the Archimedean spiral waves as a function of the initial set of insonification angles ($\alpha_i$), the geometry of the curved array of transducers and the distance (r) to the reference center (O), each local wavefront orientation satisfying the following formula:

$$\alpha_{eq,i} = \arcsin\left(\frac{r_n}{r}\sin\alpha_i\right).$$

Preferred—but non-limiting—aspects of the method according to the invention are the following:

advantageously:

the step of generating excitation signals can include generating at least two series of excitation signals at a constant repetition interval $T_P$, and the step of transforming can include transforming said at least two series of excitation signals into Archimedean spiral waves:

a first series of excitation signals allowing the obtaining of a first gathering of scattered signals (by emitting said first series of excitation signals and receiving said first gathering of scattered signals), and a second series of excitation signals allowing the obtaining of a second gathering of scattered signals (by emitting said second series of excitation signals and receiving said second gathering of scattered signals);

the step of estimating the velocity of the at least one scatterer can comprise:

receiving said first and second gatherings of scattered signals generated by scattering of said Archimedean spiral waves, delaying and summing said first gathering of scattered signals in order to generate first groups of receive beams having a respective receive angle $\beta_j$, each group of receive beams corresponding to a respective insonification angle $\alpha_i$, delaying and summing said second gathering of scattered signals in order to generate second groups of receive beams having a respective receive angle $\beta_j$, each group of receive beams corresponding to a respective insonification angle $\alpha_i$;

each of the first and second groups of receive beams can comprise a plurality of images, each image being associated with a respective pair of insonification angle $\alpha_i$ and receive angle $\beta_j$, the step of estimating the velocity of the at least one scatterer further comprising:

Doppler processing of said first and second groups of receive beams for any given pair of images of the first and second groups of receive beams having the same pair of insonification angle $\alpha_i$ and receive angle $\beta_j$ so that velocity fields are estimated for each pair of distinct spiral orientations and receive beam orientations;

the step of estimating the velocity of the at least one scatterer can further comprise the following substeps for each pair of images of the first and second groups of receive beams having the same pair of insonification angle $\alpha_i$ and receive angle $\beta_j$:

estimating of a displacement field for each corresponding pixel between the images of a given pair of images, estimating, from the displacement field, a doppler frequency shift per pixel for said given pair of images;

the step of estimating the velocity of the at least one scatterer can further comprise an algebraic inversion substep where several projections of the velocity field and their known orientation are used to estimate radial and azimuthal components of the velocity field;

the step of estimating the velocity of the at least one scatterer can further comprise a computing substep consisting in computing axial and lateral velocity components from the radial and azimuthal components of the velocity field.

BRIEF DESCRIPTION OF THE DRAWINGS

The present invention may be more completely understood in consideration of the following detailed description of various embodiments in connection with the accompanying drawings, in which.

DETAILED DESCRIPTION OF THE INVENTION

Different examples of the method and apparatus according to the invention will now be described with reference to the figures. In these different figures, equivalent elements are designated by the same numerical reference.

Figure 1:
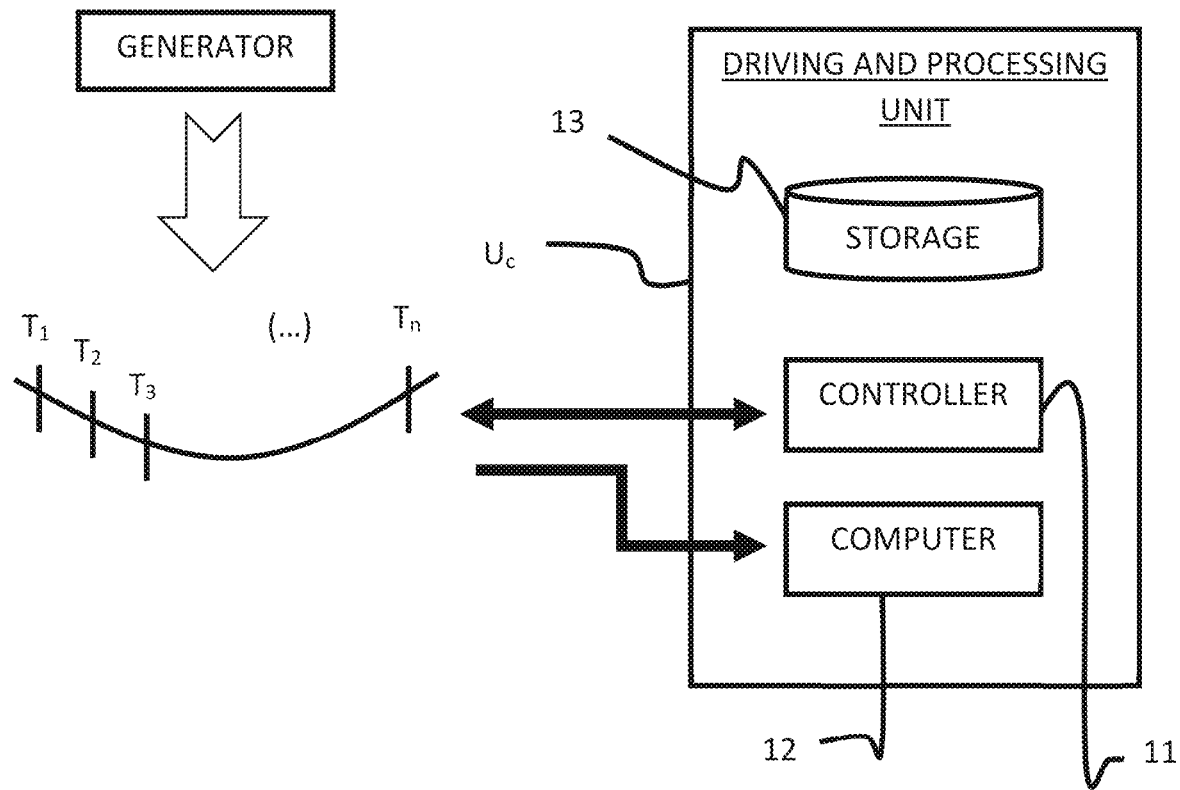
FIG. 1 is a schematic view of an apparatus for estimating the velocity vector of at least one scatterer in a medium

1. Apparatus for Estimating Radial and Azimuthal Velocities of at Least One Scatterer in a Medium An example of apparatus according to the invention is illustrated on FIG. 1.

Such an apparatus is adapted for estimating radial and azimuthal velocities of at least one scatterer in a medium. In particular, this apparatus is configured with a program for carrying out one or more of the steps of the method described below.

The apparatus comprises:
a generator for generating excitation signals,
a curved array of virtual transducers $T_1$-$T_n$ configured for:
   converting said excitation signals into Archimedean spiral waves, and for emitting said Archimedean spiral waves in a plurality of predetermined directions of propagation, each direction being defined by a respective insonification angle ($\alpha_i$),
   receiving echoes due to the scattering of the Archimedean spiral waves on the at least one scatterer, and transforming said echoes into a gathering of scattered signals,
a driving and processing unit including:
   a controller for driving the generator and the curved array of virtual transducers,
   a beamformer for beamforming the gathering of scattered signals,
   a processor for processing the beamformed gathering of scattered signals in order to determine the radial and azimuthal velocities of each scatterer.

1.1. Curved Array of Virtual Transducers

The curved array of virtual transducers $T_1$-$T_n$ comprises a set of «n» ultrasound transducers («n» being an integer equal to or above one). Each ultrasound transducer can be made of piezo-electric materials (e.g. ceramics, silicon . . . ) recovered on both sides by electrodes and on one side by several supplementary layers such as matching layers and lenses. The ultrasound transducers can be of linear or curved configuration.

If positioned linearly, delay laws are applied to the transducers for enabling the generation of ultrasound waves according to a desired geometry. In the following, said desired geometry is defined as "the curved array of virtual transducers $T_1$-$T_n$".

The curved array of virtual transducers $T_1$-$T_n$ is adapted for emitting Archimedean spiral waves (which will be defined in more details below) through the medium to be analyzed (vascular system, etc.), and to receive acoustic echoes (i.e. ultrasound waves reflected by the scatterers contained in the medium).

1.2. Driving and Processing Unit

The driving and processing unit $U_c$ is in communication (wired or wireless) with the transducers. The driving and processing unit allows:
driving the generator and the curved array of virtual transducers $T_1$-$T_n$, and
processing the data acquired by the curved array of virtual transducers $T_1$-$T_n$.

The driving and processing unit $U_c$ can be composed of one physical entity (or of different physical entities), which can be integrated to an housing including the curved array of virtual transducers, or which can be remotely located from the curved array of virtual transducers.

For instance, the driving and processing unit $U_c$ can be composed of:
one (or several) controller(s) 11, such as a Smartphone, and/or an electronic tablet (such as an IPAD®) and/or a Personal Digital Assistant (PDA), or may be of any other type known to the skilled in the art, and
one (or several) computer(s) 12 (a beamformer, a processor, etc.), such as a personal computer and/or a workstation, etc.
one (or several) storage unit 13 including at least one memory such as a Random Access Memory (RAM) and/or a Read Only Memory (ROM) and/or an USB key, etc.

In addition to the storage of the acquired/processed data, the storage unit allows storing programming code instructions intended to execute the steps of the method for estimating radial and azimuthal velocities described below.

Figure 2:
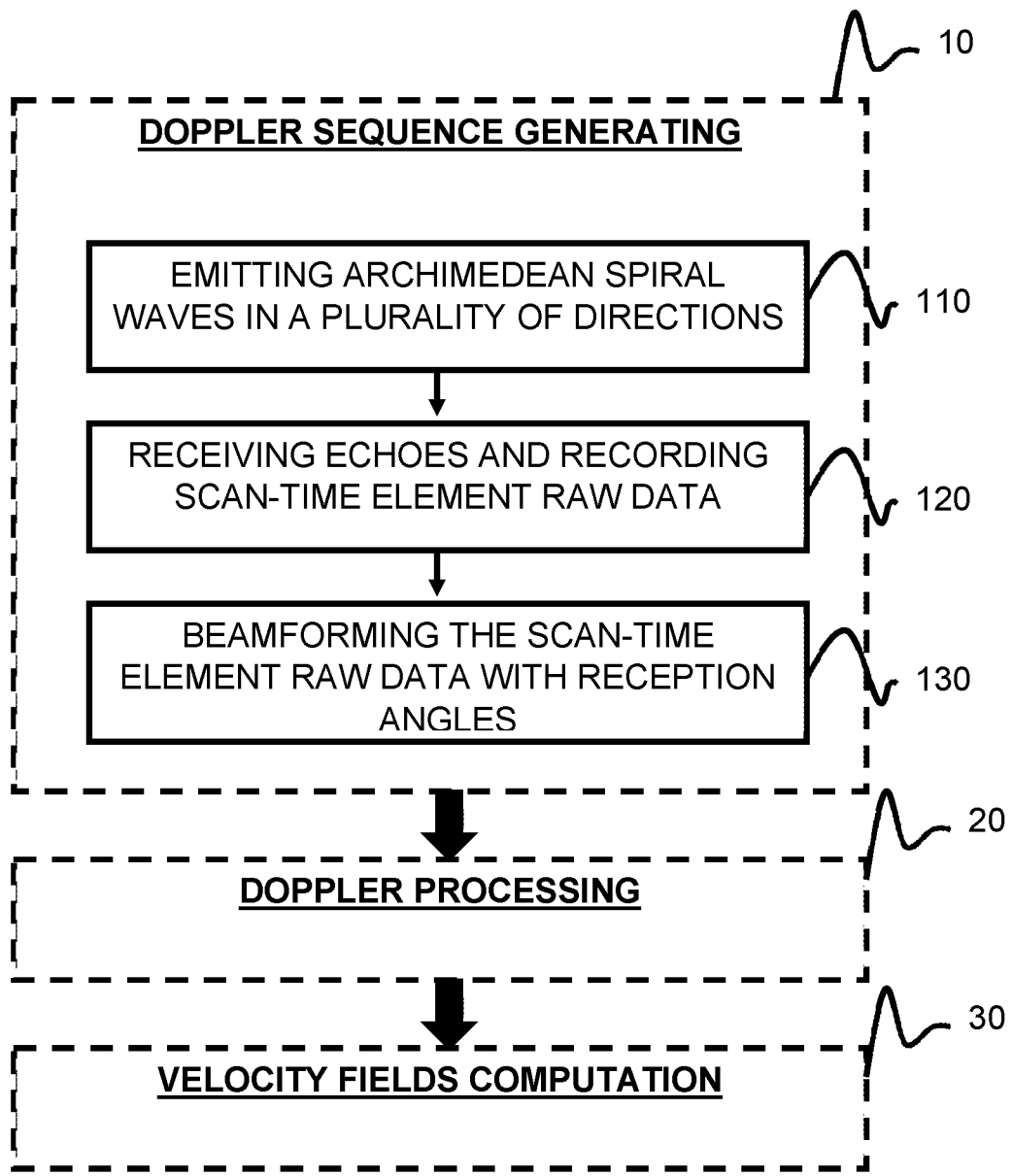
FIG. 2 is a schematic view of steps implemented in a method for estimating the velocity vector of at least one scatterer in a medium.

2. Method for Estimating Radial and Azimuthal Velocities of at Least One Scatterer in a Medium As depicted in FIG. 2, the method for estimating the velocity of at least one scatterer in a medium comprises the following steps:
a Doppler ultrasound sequence generating step 10 wherein at least two pulse-echo blocks are generated said at least two pulse-echo blocks being triggered at constant repetition intervals $T_P$, wherein the sequence generating step includes for each pulse-echo block, the following sub-steps:
   applying excitation signals to a curved array of virtual transducers which transform said excitation signals into Archimedean spiral waves that are emitted 110 in a plurality of predetermined directions of propagation, each direction being defined by a respective insonification angle ($\alpha_i$),
   receiving 120 echoes—generated by scattering of said Archimedean spiral waves by the at least one scatterer—back to the curved array of virtual transducers which transform said echoes into a gathering of backscattered signals,
   beamforming 130 the gathering of backscattered signals in order to generate a group of receive beams having a respective receive angle ($\beta_j$), said group of receive beams comprising a plurality of images, each image being associated with a respective pair of insonification angle ($\alpha_i$) and receive angle ($\beta_j$),
a Doppler processing step 20 wherein the at least two pulse-echo blocks are processed for any given pair of images of the groups of receive beams having the same pair of insonification angle ($\alpha_i$) and receive angle ($\beta_j$) in order to extract Doppler frequency shifts, a computation step 30 wherein the radial and azimuthal velocity fields are computed from the full set of pairs of distinct spiral orientations and receive beam orientations, by using the full set of Doppler frequency shifts.

2.1. General Description 2.1.1. Doppler Ultrasound Sequence Generating Step: Slow-Time/Scan-Time/Fast-Time Samples The first step of the method consists in generating a Doppler sequence.

In the context of a vector Doppler sequence, there are three relevant time-scales that can be considered formally:

the fast-time is the front-end sampling time scale that is adapted to the bandwidth of the pulse and the recording of the synthesized wave fronts and echoes propagation times, also known as time of flights, for a predefined field of view;

the scan-time is the time scale used to complete a set of projections of a given field of view; in the context of focused imaging, it is also the time scale when the left-right sweep of the imaging beams is performed; in the context of synthetic imaging it corresponds to the acquisition of the full synthetic aperture dataset; in the context of vector Doppler it also corresponds to the acquisition time scale of additional directional samples;

the slow-time is the time scale of pulse repetitions at a chosen pulse repetition frequency (PRF); the slow-time samples allow the phase (or equivalently frequency) shift computation and may constitute a statistical ensemble required to achieve the Doppler velocity field estimation for each of the directive beams; the total number of slow-time samples used for Doppler estimation is classically referred to as the ensemble length ($N_{EL}$); a minimum of two slow-time samples is typically required.

The above mentioned time scales are chosen according to the typical velocity of the scatterer such that the scatterer does not move between consecutive acquisitions of two scan-time samples and a fortiori of two fast-time samples.

The last two aforementioned time-scales may be considered in a more continuous fashion when using interpolation schemes or sliding windows (e.g. in case of uniform repartition of the scan-time samples).

Figure 3:
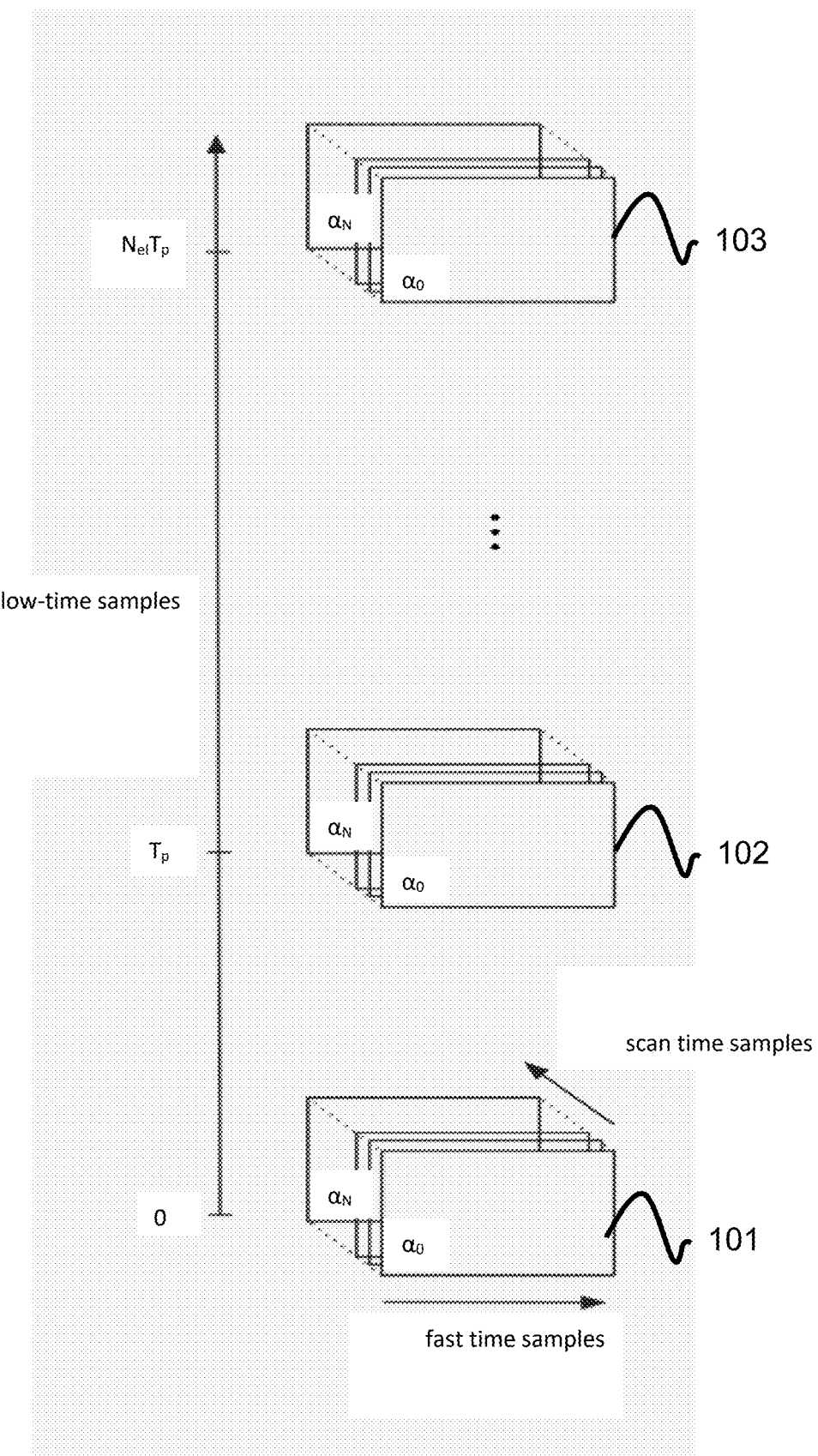
FIG. 3 is a schematic view illustrating the acquisition of a Doppler ultrasound sequence.

With regard to FIG. 3, the vector Doppler sequence is composed of multiple (at least two) slow-time samples 101, 102, 103 (i.e. pulse-echo blocks) generated periodically at a pulse repetition interval $T_P$.

More particularly, the vector Doppler sequence is composed of $N_{EL}$ (where the subscript "EL" means "Ensemble Length") slow-time samples 101, 102, 103 spaced in time by the pulse repetition interval $T_P$.

Each slow-time sample 101, 102, 103 contains a set of scan-time samples (i.e. gathering of scattered signals), which correspond to element-raw data recorded sequentially by the transducer elements, corresponding to Archimedean spiral waves tilted with insonification angle $\alpha_i$ (i=1 ... N). In particular, each slow-time sample 101, 102, 103 contains a set of images, each image being obtained for a given insonification angle $\alpha_i$ (i=1 ... N).

As mentioned above, the Doppler ultrasound sequence generating step includes the following sub-steps which are repeated periodically at the pulse repetition interval $T_P$:

the emitting 110 of Archimedean spiral waves in a plurality of predetermined directions of propagation, each direction being defined by a respective insonification angle ($\alpha_i$), the receiving and recording 120 of the set of N scan-time samples (i.e. gathering of scattered signals), and the beamforming 130 of each scan-time sample with receive angles ($\beta_j$), in order to form a set of scan time radio-frequency or in-phase quadrature beamformed data (i.e. group of receive beams having a respective receive angle).

Figure 4:
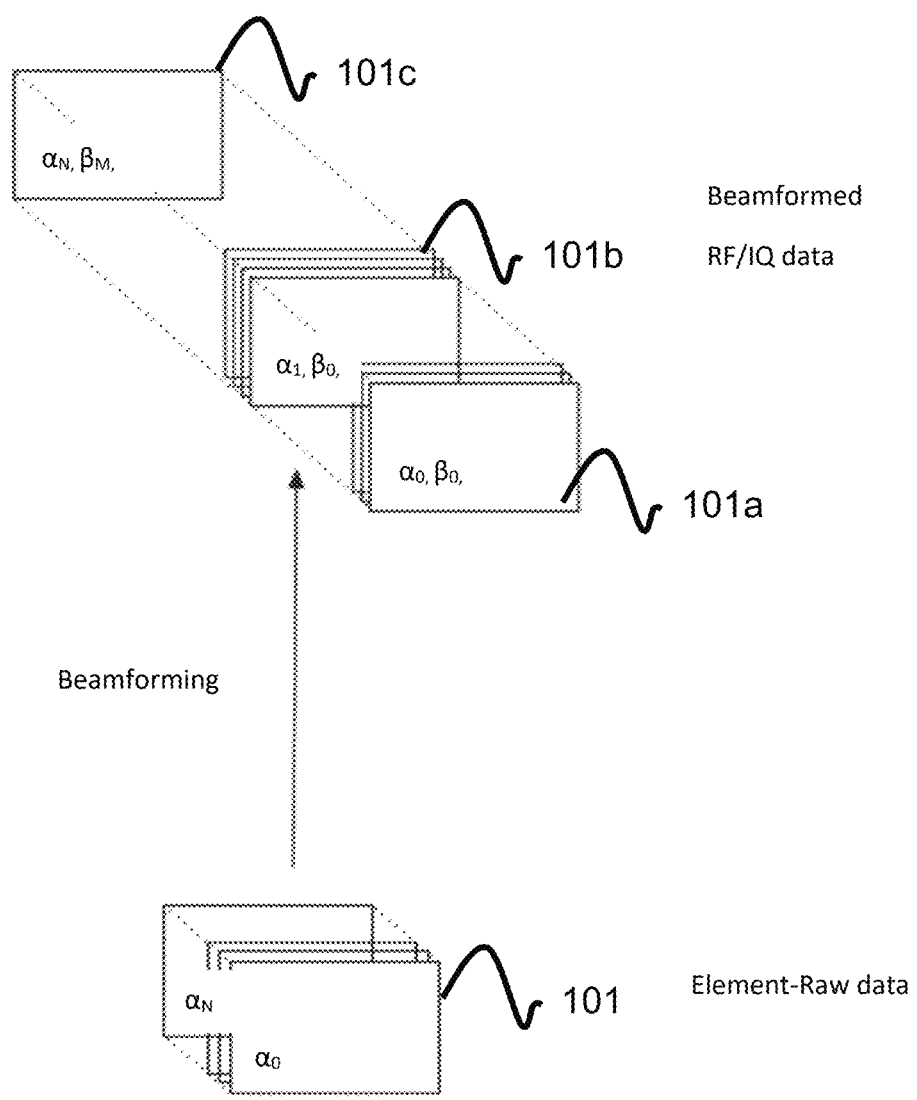
FIG. 4 is a schematic view illustrating the processing of samples of the Doppler ultrasound sequence.

As illustrated on FIG. 4, the beamforming of the N scan-time samples 101 (each associated with a respective insonification angle $\alpha_i$ (with i=1 to N)) with receive angles $\beta_j$ (with j=1 to M) allows obtaining a set of M×N beamformed IQ data 101a, 101b, 101c for each emission and reception angles pair ($\alpha_i$, $\beta_j$), where i=1 to N and j=1 to M.

2.1.2. Doppler Processing Step

The second step of the method consists in Doppler processing the slow-time samples 101, 102, 103 (i.e. pulse-echo blocks).

In particular, said at least one scatterer is moving between the acquisition of two successive slow-time samples.

During the Doppler processing step, a displacement per pixel of each moving scatterer is extracted across the slow-time samples, from the same angle pair ($\alpha_i$, $\beta_j$) of emission/reception angles. Such extraction is performed using any state-of-the-art technique, and will be described in point 2.2.4. This allows obtaining a displacement field of each moving scatterer during the Doppler ultrasound sequence.

A Doppler frequency shift per pixel for each pair of emission and reception angles ($\alpha_i$, $\beta_j$) is estimated from the displacement field.

2.1.3. Computation Step

The third step of the method consists in computing the radial and azimuthal velocity fields of each scatterer (using the pairs of emission and reception angles ($\alpha_i$, $\beta_j$)) by using the Doppler frequency shift.

More particularly, the computing step comprises the following sub-steps:

per radial coordinate, forming a Doppler linear operator that relates the Doppler frequency shift to the radial and azimuthal velocity fields; such an operator depends on the local wavefront angle of each transmitted Archimedean spiral wave, and per radial coordinate, solving the corresponding linear system of equations using standard linear algebra techniques and recovering the radial and azimuthal velocity components.

2.1.4. Advantages of the Proposed Method

The main contribution of the proposed method resides in the use of Archimedean spiral waves in order to ensure directivity in emission.

Indeed, it will be demonstrated below that an Archimedean spiral wave emitted with a specific emission angle defines a wavefront whose local angle can be expressed as a function of the radial coordinate of a pixel of interest. In other words, Archimedean spirals are highly directive in polar coordinates, like plane waves in Cartesian coordinates, and such a directivity can be exploited in VFI for estimating radial and azimuthal velocity components.

These radial and azimuthal components are expressed in a polar coordinate system.

In a final step, one can perform a conversion from polar to Cartesian components in order to obtain lateral and axial velocity components. Then a scan conversion from polar to Cartesian coordinates is possible to express such components in a Cartesian coordinate system.

Another advantage resides intrinsically in the use of Archimedean spiral insonifications as compared to other diverging insonifications (incl. plane waves) in a convex probe configuration. In the case of a virtual array of transducers matching the real array of transducers, the Archimedean spirals are the best choice in terms of single transducer element directivity across the whole transducer array. As a consequence, the full convex field of view can be exploited.

2.2. Detailed Description

Different aspects of the method according to the invention will now be described in more details.

In the following, the curved array of virtual transducers T1-Tn is considered as being composed of a set of virtual transducers distributed along an arc of radius $r_n$ (usually denoted as the convex radius of the probe). The space between two adjacent virtual transducers is denoted as p, recalled as pitch.

2.2.1. Emission of an Archimedean Spiral Wavefront

The emission of an Archimedean-spiral wavefront with the curved array of virtual transducers T1-Tn is performed by applying a linear delay law profile to the virtual transducers.

More precisely, if one assumes that the curved array of virtual transducers T1-Tn is composed of n virtual transducers, spaced along an arc of radius $r_n$, with pitch (inter-element distance) p and a speed of sound of c, the linear delay profile is defined as:

$$\forall i \in \{1, \ldots n\}, \tau_i(\alpha) = \frac{(i-1)p}{c}\sin\alpha,.$$

The angle $\alpha$ is coined as the steering angle. Hence, each virtual transducer of the curved array emits a short ultrasound wave after a delay given by the Equation above.

2.2.2. Archimedean Spiral Based Beamforming

Once the wavefront is emitted, it propagates within the medium and gets reflected when it encounters local variations of acoustic impedance, i.e. density and speed of sound (scatterer). Such variations are modelled through the tissue reflectivity function $\gamma(r)$ at a considered target location $r=[r,\theta]$ in the tissue.

The scattered waves propagate back to the virtual transducers and corresponding echoes are therefore recorded. We denote as $m_i(t)$ the signal recorded by the i-th virtual transducer.

The process of beamforming amounts to reconstructing an estimate of the reflectivity of the medium $\hat{\gamma}(r)$ from the recorded signals $m_i$.

The usual delay-and-sum (DAS) estimate is built as follows:

$$\hat{\gamma}(r, \alpha) = \sum_{j=1}^{n} a_j m_j(t_{Tx}(r, \alpha) + t_{Rx,j}(r)),$$

where $t_{Tx}$ and $t_{Rx}$ account for the global transmit and receive delays, respectively, and $(a_i)_{i=1, \ldots, n}$ are the apodization weights.

Figure 5:
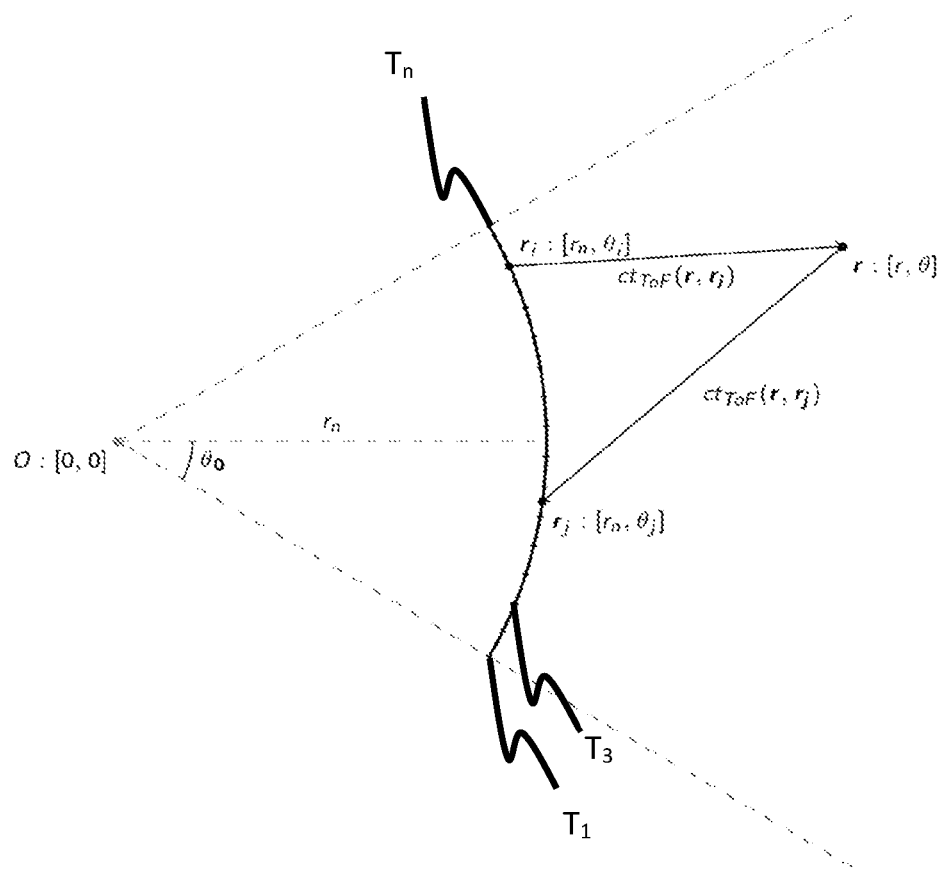
FIG. 5 is a schematic view illustrating a convex-array imaging configuration.

A polar coordinate system is adopted where the origin O is located at the center of the curved array of virtual transducers T1-Tn, such that the virtual transducers are located at $r_i=[r_n,\theta_i]$, where $r_n$ denotes the convex radius of the curved array of virtual transducers T1-Tn, as illustrated on the FIG. 5. With such a coordinate system, the delay profile may be expressed as a function of the transducer elements coordinates:

$$\forall i \in \{1, \ldots n\}, \tau_i(\alpha) = \frac{r_n(\theta_i - \theta_0)}{c}\sin\alpha,$$

The receive delay corresponds to a simple time-of-flight computation and is quite straightforward to express as follows:

$$t_{Rx,j}(r) = t_{ToF}(r, r_j) = \frac{\|r - r_j\|_2}{c},$$

for a transducer element located at $r_j$ and a considered target location r, as illustrated on the FIG. 5.

The global transmit delay is defined as the instant when the considered target location is first hit by the pulsed wave emitted by any of the emitting transducer elements of the array. In other words, it is derived from the minimization of both the transmit delay and the transmit time-of-flight to the considered target location in the medium:

$$t_{Tx}(r, \alpha) = \min_i(\tau_i(\alpha) + t_{ToF}(r, r_i)),$$

By expanding the terms and offsetting the constant delay with a new time origin, the minimization equation can be rewritten as:

$$ct_{Tx}(r, \alpha) = \min_{\theta_i}\left(\sqrt{r^2 + r_n^2 - 2rr_n\cos(\theta_i - \theta)} + r_n\theta_i\sin\alpha\right),$$

The resolution of the latter minimization is left to the skilled man. Additional details about the method will be presented in the theoretical section (3.2.1). As a consequence, the global transmit delay to the point located at $r=[r, \theta]$ can be expressed as:

$$ct_{Tx}(r, \alpha) = \left(\sqrt{r^2 - r_n^2\sin^2\alpha} - r_n\cos\alpha + r_n\left(\theta - \alpha + \arcsin\left(\frac{r_n}{r}\sin\alpha\right)\right)\sin\alpha\right).$$

In the wavefront approximation, this equation may be seen as a parametric equation of the transmit wavefront.

In order to derive a way to perform vector flow imaging in polar coordinates, the inventors' idea is to identify waves that are highly directive in a polar space like plane waves in the Cartesian space. The following demonstration shows that Archimedean spirals waves have such a property of a well-defined direction in a polar space.

The direction of the wavefront is the direction in which the global transmit delay increases most (i.e. normal to the direction in which it is constant). By computing the transmit delay gradient relative to the polar coordinates, this direction can be explicitly determined. The global transmit delay gradient is computed using the polar gradient expression:

$$\nabla t_{Tx} = \frac{\partial t_{Tx}}{\partial r}\vec{u}_r + \frac{1}{r}\frac{\partial t_{Tx}}{\partial \theta}\vec{u}_\theta$$

The obtained gradient expression after simplification comes down to:

$$c\nabla t_{Tx} = \sqrt{1 - \frac{r_n^2}{r^2}\sin^2\alpha}\,\vec{u}_r + \frac{r_n}{r}\sin\alpha\,\vec{u}_\theta$$

Formally, the concept of equivalent steering angle can be introduced with the following equation:

$$\alpha_{eq} = \arcsin\left(\frac{r_n}{r}\sin\alpha\right),$$

such that $$\sin\alpha_{eq} = \frac{r_n}{r}\sin\alpha \text{ and } \cos\alpha_{eq} = \sqrt{1 - \frac{r_n^2}{r^2}\sin^2\alpha}.$$

so that the substitution in the global transmit delay gradient expression yields:

$$c\nabla t_{Tx} = \cos\alpha_{eq}\,\vec{u}_r + \sin\alpha_{eq}\,\vec{u}_\theta$$

Hence, the expression of the global transmit delay gradient shows a specifically steered orientation $\alpha_{eq}$ relative to the local polar coordinates.

Figure 6:
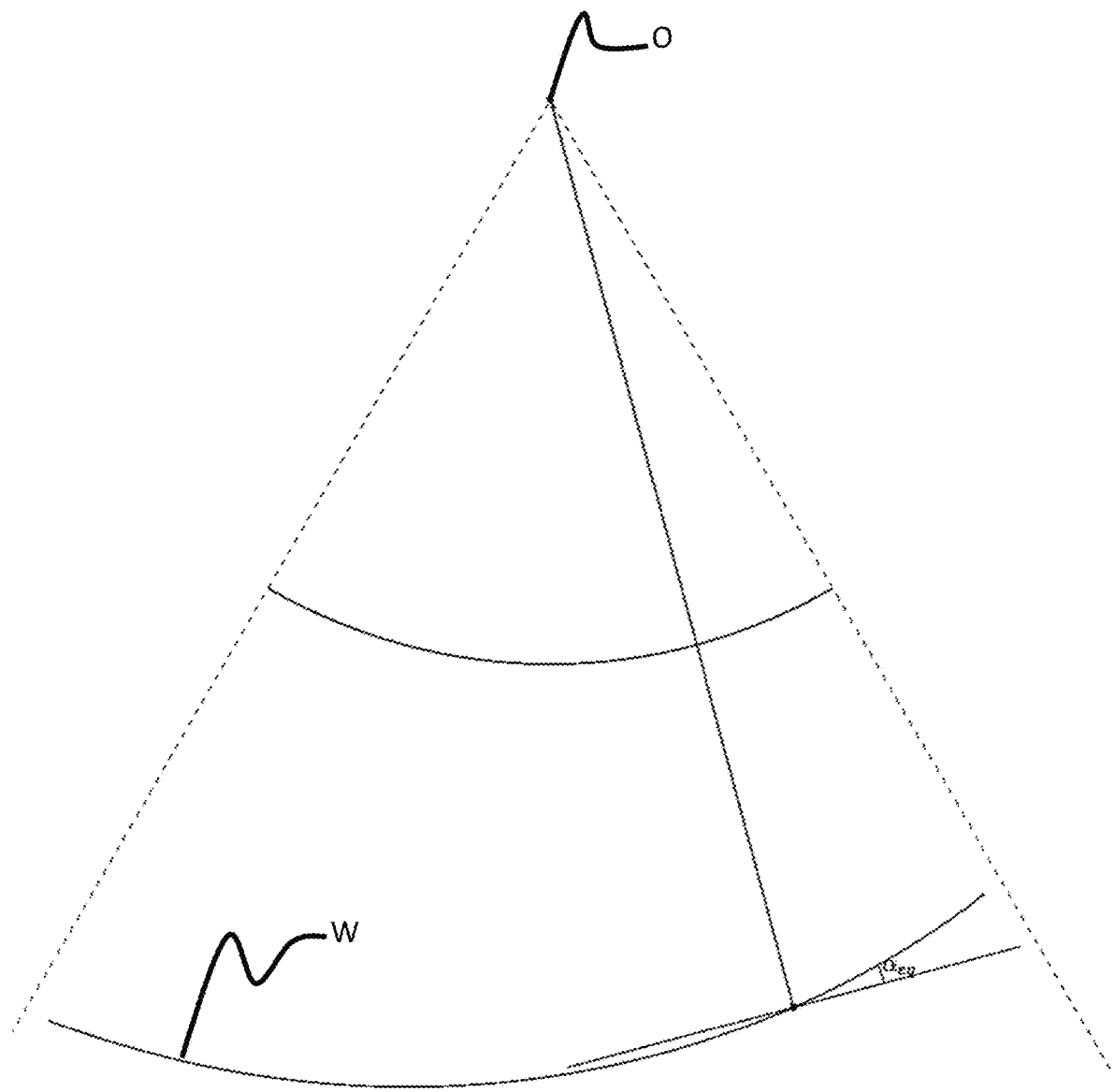
FIG. 6 is a schematic view illustrating an Archimedean-spiral wavefront.

Archimedean-spiral wavefronts W are highly directive in polar coordinates like plane waves in Cartesian coordinates, as illustrated in FIG. 6.

The idea of the inventors is to exploit such a directivity to extract radial and azimuthal velocity components from their projections along the wavefront, as explained below.

2.2.3. Archimedean Spiral Based Beamforming at a Given Reception Angle

The previous Section shows that transmit directivity is achieved by means of tilted Archimedean-spiral waves.

In order to achieve directivity in receive, the inventors rely on techniques already known in the literature and developed for vector flow imaging with a linear array.

In one embodiment, the inventors propose using separate subapertures with desired receive angles, as described in the document titled "*Ultrafast compound imaging for 2-D motion vector estimation: application to transient elastography*", M. Tanter, J. Bercoff, L. Sandrin, and M. Fink, IEEE Trans. Ultrason. Ferroelectr. Freq. Control, vol. 49, no. 10, pp. 1363-1374, October 2002.

In another embodiment, one can beamform the data as described in previous Section and later filter the 2D spectrum of the beamformed data depending on the desired angle, as suggested by Stähli et al. (see document titled "*Improved forward model for quantitative pulse-echo speed-of-sound imaging*", P. Stähli, M. Kuriakose, M. Frenz, and M. Jaeger, Ultrasonics, vol. 108, p. 106168, December 2020).

Such beamforming techniques allows increasing the size of the beamforming data cube since we now have $\tilde{\gamma}(r, \alpha_{eq}, \beta)$, with $\beta$ being the reception angle.

2.2.4. Displacement Extraction and Doppler-Frequency-Shift Estimation

In US imaging, displacement extraction is performed by analyzing variations in IQ or RF images along slow-time.

Hence, all the techniques first start with the transmission/reception and beamforming of a set of IQ images, denoted as slow time samples. Such images are usually acquired with a constant rate denoted as the pulse-repetition frequency and we recall them as slow-time samples.

In order to extract Doppler frequency shifts from RF or IQ image slow-time samples $(\gamma_i)_{i \in N_{EL}}$, many techniques have been developed in the literature. Nevertheless, the different techniques share the common idea of tracking the translation of recorded backscattered signals between consecutive pulses.

The different methods mainly depend on the nature of the received backscattered echoes (RF or IQ, narrowband or broadband).

A well-known technique consists in computing the phase-shift using the lag-1 temporal autocorrelation $R_1$ usually denoted as Kasai autocorrelation (or 1D autocorrelation), as described by Angelsen (see document titled "*Instantaneous Frequency, Mean Frequency, and Variance of Mean Frequency Estimators for Ultrasonic Blood Velocity Doppler Signals*", B. A. J. Angelsen, IEEE Transactions on Biomedical Engineering, vol. BME-28, no. 11. pp. 733-741, 1981, doi: 10.1109/tbme.1981.324853.) and Kasai et al. (see document titled "*Real-Time Two-Dimensional Blood Flow Imaging Using an Autocorrelation Technique*", C. Kasai and K. Namekawa, IEEE 1985 Ultrasonics Symposium. 1985, doi: 10.1109/ultsym.1985.198654). However other Doppler estimators known from the skilled person can also be considered equivalently like for instance the 2D autocorrelator (better known today as the Loupas estimator) or the cross-correlator (see document titled "*An axial velocity estimator for ultrasound blood flow imaging, based on a full evaluation of the Doppler equation by means of a two-dimensional autocorrelation approach*", T. Loupas, J. T. Powers, and R. W. Gill, IEEE Transactions on Ultrasonics, Ferroelectrics and Frequency Control, vol. 42, no. 4. pp. 672-688, 1995, doi: 10.1109/58.393110).

Hereafter, the phase-based estimation technique described by Kasai et al. is detailed. Formally, consider that we have access to $N_{EL}$ (ensemble length) consecutive slow-time samples, acquired with a time interval $T_P$, the pulse repetition period, with $T_P = 1/f_P$ where $f_P$ is the pulse repetition frequency (PRF), the Doppler phase shift $\Delta\Phi \in \mathbb{R}^{N_r \times N_\theta}$ is estimated from the following formula:

$$\Delta\Phi = \angle R_1 \text{ with } R_1 = \sum_{k=1}^{N_{EL}-1} \gamma_{k+1}\gamma_k^*$$

Note that the ensemble length can be down to 2 consecutive frames. The estimated phase shift and the Doppler frequency shift $\delta f_p$ are linked by the following equation:

$$2\pi\delta f_p \times T_P = \Delta\Phi$$

In addition, the module of the velocity projected along the propagation of the ultrasound beam can be related to the Doppler frequency shift as:

$$v = -c\frac{\delta f_p}{2f_0} = -c\frac{\Delta\Phi}{4\pi T_P f_0}.$$

Hence, there exists a maximal velocity associated with the given PRF corresponding to a maximal phase shift of $\pm\pi$ between consecutive signals which can be derived from the above equation as:

$$v_{max} = \frac{\pi c}{4\pi T_P f_0} = \frac{\lambda}{4T_P}.$$

The skilled person can deduct from the above formulae the importance of having a high PRF in order to have $v_{max}$ as high as possible.

2.2.5. Estimation of Radial and Azimuthal Velocities

Using simple geometrical projections, a similar relationship to plane-wave imaging can be expressed, but pixel-wise and in polar coordinates, as follows:

$$c\frac{\Delta f_{p_{kl}}}{f_0} = v_{r_{kl}}(\cos\alpha_{eq_{kl}} + \cos\beta) + v_{\theta_{kl}}(\sin\alpha_{eq_{kl}} + \sin\beta),$$

$$k, l \in \{1, \ldots, N_r\} \times \{1, \ldots, N_\theta\},$$

where $v_{r_{kl}}$ and $v_{\theta_{kl}}$ denote the radial and azimuthal velocities, $\alpha_{eq_{kl}}$ and $\beta$ are the equivalent transmit and receive angles, and $N_r$ and $N_\theta$ account for the number of pixels in radial and azimuthal dimensions.

Consider a set of N angles in emission $\alpha_i$, i=1, ..., N and M angles in reception $\beta_j$, j=1, ..., M, we can build the following linear system of equations $$A_k v_{kl} = u_{kl}, k, l \in \{1, \ldots, N_r\} \times \{1, \ldots, N_\theta\},$$

where $v_{kl} \in \mathbb{R}^2$ is the vector of velocities and $u_{kl} \in \mathbb{R}^{NM}$ contains the Doppler frequency components for each transmit and receive angle and $A_k \in \mathbb{R}^{NM \times 2}$ is the matrix of equivalent steering angles such that $$c\frac{\Delta f_{p_{kl}}}{f_0} = v_{r_{kl}}(\cos\alpha_{eq_{kl}} + \cos\beta) + v_{\theta_{kl}}(\sin\alpha_{eq_{kl}} + \sin\beta),$$

$$k, l \in \{1, \ldots, N_r\} \times \{1, \ldots, N_\theta\},$$

For $NM \geq 2$ such a linear system can be well-posed and standard least-squares methods can be exploited to recover the velocity components:

$$v_{kl} = A_k^{-1} u_{kl}.$$

It can be noticed that the matrix $A_k$ is defined for every depth and is therefore not unique, as in plane-wave imaging. Hence, many more inversions are needed which make the algorithm more computationally costly.

The axial and lateral velocities are then deduced from the radial and angular velocities using standard conversion formulas given below $$v_x = v_r \sin\theta + v_\theta \cos\theta \text{ and } v_z = v_r \cos\theta - v_\theta \sin\theta.$$

The skilled person will observe that $v_x \in \mathbb{R}^{N_r \times N_\theta}$ and $v_z \in \mathbb{R}^{N_r \times N_\theta}$ are still expressed on a polar grid.

A final step of the method can consist in performing a scan conversion from a uniform polar grid to a uniform Cartesian grid:

$$v_x^c = f(v_x, \Omega_c, \Omega_p) \text{ and } v_z^c = f(v_z, \Omega_c, \Omega_p),$$

where $\Omega_c$ and $\Omega_p$ denote the polar and Cartesian grids and f performs the scan-conversion. Standard techniques exploit 2D interpolation methods, e.g. bilinear or bicubic interpolation, to evaluate the values on the regular grids from the values on the irregular one.

2.3. Conclusions

The above described vector-flow imaging technique is adapted for sectorial imaging. The proposed method exploits the directivity of steered Archimedean-spiral wavefronts in the polar space in order to extract the radial and azimuthal velocity components from their projections along the directions of the transmit and receive beams.

The medium is sequentially insonified with different steered Archimedean spiral wavefronts. The displacement fields for each angle is computed and a system of linear equations that relates such fields to the radial and azimuthal components of the velocity flow is built. Solving such a system allows recovering the two dimensional flow.

The proposed method paves the way to ultrafast vector flow imaging in convex array configurations. It may be of major interest for several clinical applications where tortuous flows are encountered in deep abdominal organs e.g. portal vein flow imaging of cirrhotic patients or characterization of abdominal aortic aneurysm.

3. Theory Relative to the Invention

3.1. Introduction

Non-invasive visualization and measurements of flow dynamics using ultrasound (US) is considered to be of major clinical importance e.g. to highlight abnormal vascular conditions.

Standard techniques, e.g. color-flow imaging, continuous-wave Doppler and pulsed-wave Doppler, offer one dimensional views and measurements of the flow along the axial dimension. Such methods suffer from an intrinsic methodological flaw due to their dependency to the angle between the direction of the flow and the one of the US beam. This may be problematic in cases where one may encounter tortuous vasculature, e.g. at carotid bifurcation.

Vector flow imaging (VFI) methods solve this problem by providing both axial and lateral components of the velocity flow.

Different techniques have been described in the literature such as multi-beam Doppler [1], inter-frame speckle tracking [2] or transverse oscillation [3]. See [4], [5] for an exhaustive review. With the massive adoption of ultrafast US imaging in the community, multi-beam methods have drawn significant interest recently. Indeed, the idea is to benefit from both the high directivity and the unfocused aspect of plane waves to derive vector flow information from projections along the direction of the transmit beam at high frame rates, therefore reducing the potential for aliasing [6].

While VFI methods have been extensively studied in linear array configurations, the literature is lacking regarding convex array geometries. VFI methods in convex array configurations may be of significant interest for various applications such as portal vein imaging. In this paper, we suggest a novel VFI technique in convex-array configurations based on the transmission of steered Archimedean-spiral wavefronts. We demonstrate that Archimedean spirals are highly directive in a pseudo-polar space which allows us to extract radial and azimuthal velocity components from projections along the propagation direction of the wavefront. In addition, we show that using such wavefronts permits to draw a clear analogy with VFI methods developed in plane-wave imaging. Hence, the proposed algorithm, largely inspired from the one derived in [6], is based on the sequential transmission of several steered Archimedean-spiral wavefronts. We deduce the displacement fields associated with each steering angle and build a linear system of equations relating these fields to the corresponding projections of the radial and azimuthal velocity components.

Solving such a system using simple linear algebra allows us to obtain per pixel estimates of both velocity components, which can be easily transformed to axial and lateral velocity components if needed.

Figure 7:
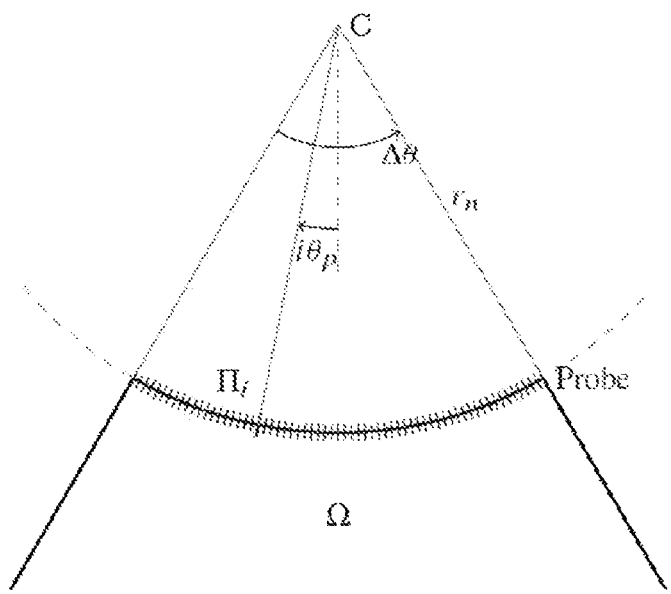
FIG. 7 is a schematic view of a convex array configuration.

3.2. Theoretical Considerations
3.2.1. Archimedean-Spiral-Based Imaging We consider the imaging configuration displayed on FIG. 7 where a convex probe defined in a polar coordinate system by its convex radius $r_n$, its angle pitch $\theta_p$ and the number of transducer elements $N_t=2N+1$, is used to insonify the medium $\Omega$. Each transducer element $\pi_i$ is located at $(r_n; i\theta_p)$, for i between −N and N, and we define the angle span of the probe as $\Delta\theta=N_t\theta_p$. The medium of interest $\Omega$, supposed to be homogeneous with constant speed of sound c, is characterized by:

$$\Omega=\{(r,\theta)|r\geq r_n, \theta\in[-\pi,\pi].\}$$

Archimedean-spiral-based imaging is performed as described in the detailed description (section 2.2). The medium is insonified with Archimedean spiral wavefronts characterized by their steering angle $\alpha$. We deduce the global transmit delay for such a wavefront by minimizing an equation:

$$ct_{Tx}(r,\alpha) = \min_{\theta_i}\left(\sqrt{r^2+r_n^2-2rr_n\cos(\theta_i-\theta)}+r_n\theta_i\sin\alpha\right),$$

The resolution of this minimization problem involves the zeroing of the derivative respective to $\theta_i$ and requires the resolution of a second order polynomial equation leading to the following identity:

$$\cos(\theta_i^*-\theta)=\cos(\alpha-\alpha_{eq})$$

where $\theta_i^*$ is the argument solution to the minimization problem and $\alpha_{eq}$ the equivalent angle defined such that:

$$\alpha_{eq}=\arcsin\left(\frac{r_n}{r}\sin\alpha\right),$$

Note that since the radius r in the field of view is always larger than the probe radius $r_n$ the absolute value of the equivalent angle $\alpha_{eq}$ is always smaller than the initial delay angle $\alpha$ so that:

$$\text{sgn}(\alpha-\alpha_{eq})=\text{sgn}(\alpha)$$

Looking at the configuration depicted in FIG. 5, one can notice that when $\theta_i$ is larger than $\theta$, $\alpha$ is negative so that:

$$\theta_i^*=\theta-\alpha+\alpha_{eq}$$

By substituting the identity in the minimization equation, one can obtain after simplification the following expression for the global transmit delay:

$$ct_{Tx}(M,\alpha)=r\cos\alpha_{eq}-r_n\cos\alpha+r_n(\theta-\alpha+\alpha_{eq})\sin\alpha$$

where $M=(r,\theta)$.

Replacing $\alpha_{eq}$ by its expression, we can get the global transmit delay expression as written in the detailed description (section 2.2):

$$ct_{Tx}(r,\alpha)=\left(\sqrt{r^2-r_n^2\sin^2\alpha}-r_n\cos\alpha+r_n\left(\theta-\alpha+\arcsin\left(\frac{r_n}{r}\sin\alpha\right)\right)\sin\alpha\right).$$

A first order Taylor expansion in $\alpha$ of the global transmit delay expression yields:

$$ct_{Tx}(M,\alpha)\approx r-r_n+r_n\theta\alpha$$

Fixing the global transmit delay, we obtain a parametric equation for the wavefront corresponding to a Archimedean spiral equation of the shape $r=a+b\theta$:

$$r\approx r_n+ct_{Tx}+r_n\theta\alpha$$

We consider that we emit $N_a$ Archimedean spirals with steering angle $\alpha_k$ (supposed to be all different) for k between 1 and $N_a$. For each steering angle, we reconstruct the delay-and-sum (DAS) estimate $\Gamma_k\in\mathbb{C}^{N_r\times N_\theta}$ of the medium tissue-reflectivity function, where $N_r\in\mathbb{N}$ and $N_\theta\in\mathbb{N}$ account for the number of pixels in the radial and azimuthal directions respectively.

The DAS estimate $\Gamma_{klu}$ is given by:

$$\Gamma_{klu}=\sum_{i=-N}^{N}a_i(M_{lu})m_i(\tau(M_{lu},\Pi_i,\alpha_k)), \quad (2)$$

where $m_i(t)$ are the backscattered echoes recorded by the transducer $\pi_i$, $M_{lu}$ is the point corresponding to the pixel of interest, $a_i(M_{lu})$ are the receive apodization weights and $(\zeta^{-1}(M_{lu},\pi_i,\alpha_k)$ is the round-trip time of flight between $M_{lu}$ and $\pi_i$ expressed as:

$$\tau\left(M_{lu},\prod_i,\alpha_k\right)=t_{Tx}(M_{lu},\alpha_k)+\frac{\left\|\prod_i M_{lu}\right\|}{c}, \quad (3)$$

where $\|\cdot\|$ denotes the Euclidean distance.

3.2.2. Vector Flow Imaging

Physically speaking, the direction of a wavefront is defined as the normal direction to isophase surfaces, or equivalently as the direction of the wave field phase gradient, also known as the wave vector. Since the transmit time-of-flight is known explicitly, the transmit phase gradient can be derived explicitly at any given point. The transmit phase gradient is computed using the polar gradient expression:

$$\nabla\varphi=\frac{\partial\varphi}{\partial r}\vec{u}_r+\frac{1}{r}\frac{\partial\varphi}{\partial\theta}\vec{u}_\theta$$

where the wavefront phase is linked to the transmit time-of-flight. Assuming a monochromatic wave, for the sake of simplicity, both are linked by the following equation:

$$\varphi=\omega t_{Tx}(r,\theta,\alpha)$$

The obtained gradient expression after simplification is:

$$\nabla\varphi=\frac{\omega}{c}\left(\sqrt{1-\frac{r_n^2}{r^2}\sin^2\alpha}\,\vec{u}_r+\frac{r_n}{r}\sin\alpha\vec{u}_\theta\right)$$

Formally, the concept of equivalent steering angle can be introduced with the following equation:

$$\alpha_{eq}=\arcsin\left(\frac{r_n}{r}\sin\alpha\right),$$

such that $$\sin\alpha_{eq}=\frac{r_n}{r}\sin\alpha \text{ and } \cos\alpha_{eq}=\sqrt{1-\frac{r_n^2}{r^2}\sin^2\alpha}.$$

so that the substitution in the phase gradient expression yields:

$$\vec{k} = \nabla \varphi = \frac{\omega}{c}\left(\cos\alpha_{eq}\vec{u}_r + \sin\alpha_{eq}\vec{u}_\theta\right)$$

Hence, the expression of the wave vector shows a specifically steered orientation $\alpha_{eq}$ relative to the local polar coordinates.

Figure 8:
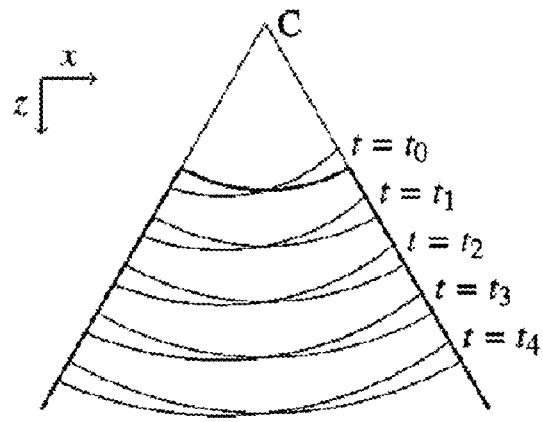
FIG. 8 is a representation of an Archimedean spiral wave in different spaces.
Figure 8:
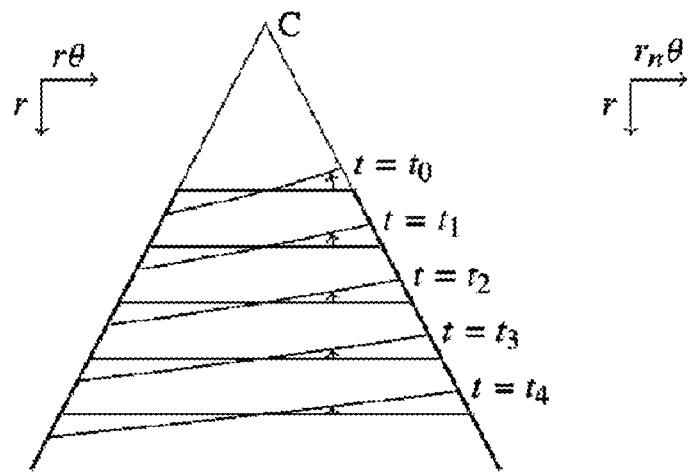
Figure 8:
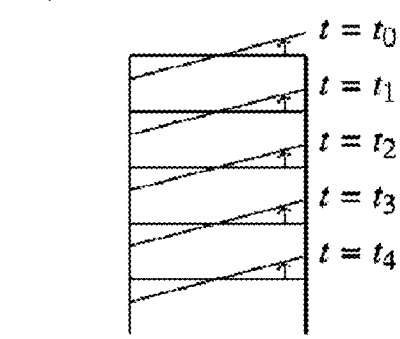

The pressure field (6) corresponds to the one of a wavefront steered by an angle $\alpha_{eq}$. Such a wavefront is flattening with depth as illustrated by FIG. 8.

Archimedean-spiral wavefronts are highly directive in polar coordinates like plane waves in Cartesian coordinates. Hence, the idea is to exploit such a directivity to extract radial and azimuthal components from their projections along the wavefront, as explained below. Consider that we acquire $N_e$ consecutive sets of $N_a$ angles, with a pulse repetition period $T_{PR}$, from which we compute the DAS estimates $\hat{\Gamma}_{ek}$, for k between 1 and $N_a$ and e between 1 and $N_e$. We compute the displacement using the Kasai autocorrelation algorithm [9] as:

$$\Delta\Phi_{ek} = \angle R_{1_{ek}}, \quad R_{1_{ek}} = \sum_{i=1}^{N_l-1} \hat{\Gamma}_{(i+e)k}\hat{\Gamma}^*_{(i+l+e)k}, \quad (8)$$

where $N_l$ accounts for the ensemble length, e varies between 1 and $N_e-N_l$. * denotes the complex conjugate and $\angle \bullet$ accounts for the angle operation. The pixelwise estimated phase shift $\Delta\Phi_{eklu}$ and the corresponding Doppler frequency shift $\Delta f_{p_{eklu}}$ are related by:

$$\Delta f_{peklu} = \frac{\Delta\Phi_{eklu}}{2\pi T_{PR}}, \quad (9)$$

which allows us to finally relate the Doppler frequency shift to the projection of the velocity on the direction of the US beam as:

$$v_{eklu} = v_{r_{elu}}(\cos\alpha_{eqkl}+1) + v_{\theta_{elu}}\sin\alpha_{eqkl} = c\frac{\Delta f_{p_{eklu}}}{2f}. \quad (10)$$

where the receive beams are assumed to have a zero degree steered orientation for the sake of simplicity. Hence, the Doppler frequency shift $\Delta f_{p_{eklu}}$ for k between 1 and $N_r$, l between 1 and $N_e$ and u between 1 and $N_a$, induced by a displacement within the medium is expressed as:

$$\Delta f_{p_{eklu}} = \frac{f}{2c}\left(v_{r_{elu}}(\cos\alpha_{eqkl}+1) + v_{\theta_{elu}}\sin\alpha_{eqkl}\right), \quad (11)$$

$e, k, l, u \in \{1, \ldots, N_e-N_l\}\times\{1, \ldots, N_a\}\times\{1, \ldots, N_r\}\times\{1, \ldots, N_\theta\},$ where f denotes the transmit frequency and $v_{r_{elu}}$ and $v_{\theta_{elu}}$ are the radial and azimuthal velocities at a pixel (l, u) on the polar grid and a time instant $e*T_{PRF}$.

Equation (11) allows us to express the following linear system of equations:

$$\frac{2c\Delta f_{p_{elu}}}{f} = A_l v_{elu}, \quad (12)$$

where $\Delta f_{p_{elu}} = (\Delta f_{p_{elu}}, \ldots, \Delta f_{p_{N_a lu}}) \in \mathbb{R}^{N_a}$,
$v_{elu} = (v_{r_{elu}}, v_{\theta_{elu}}) \in \mathbb{R}^2$ and $A_l \in \mathbb{R}^{N_a\times 2}$ is defined as follows:

$$A_l = \begin{bmatrix} \cos\alpha_{eq1l}+1 & \sin\alpha_{eq1l} \\ \cos\alpha_{eq2l}+1 & \sin\alpha_{eq2l} \\ \vdots & \vdots \\ \cos\alpha_{eqN_a l}+1 & \sin\alpha_{eqN_a l} \end{bmatrix}. \quad (13)$$

For $N_a \geq 2$, the linear system (12) is well posed and which can be solved using standard linear algebra methods, e.g. by computing the Moore pseudo-inverse.

In a final step, the axial and lateral velocity components can be deduced from the radial and azimuthal velocities as follows:

$$\begin{cases} v_{x_{elu}} = v_{r_{elu}}\sin\theta_u + v_{\theta_{elu}}\cos\theta_u \\ v_{z_{elu}} = v_{r_{elu}}\cos\theta_u + v_{\theta_{elu}}\sin\theta_u \end{cases}. \quad (14)$$

The skilled person will have understood that many modifications may be provided to the invention described earlier without materially departing from the new teachings and advantages described here. Therefore, all the modifications of this type are intended to be incorporated inside the scope of the appended claims.

The invention claimed is:

1. An apparatus configured to estimate a velocity of at least one scatterer in a medium, wherein the apparatus comprises:
   a generator configured to generate excitation signals,
   a curved array of virtual transducers configured to transform said excitation signals into Archimedean spiral waves and configured to:
   emit said Archimedean spiral waves in a plurality of predetermined directions of propagation defined by a set of insonification angles $\alpha_i$, wherein a curvature of said curved array of virtual transducers defines a reference center and a radius of curvature $r_n$, and to receive, from said at least one scatterer, scattered signals generated by scattering of said Archimedean spiral waves emitted from said curved array of virtual transducers,
   a driving and processing unit configured to drive the generator and the curved array of virtual transducers, and configured to estimate the velocity of the at least one scatterer,
   wherein axial and lateral velocity components are estimated using a set of local wavefront orientations $\alpha_{eq,i}$ of the Archimedean spiral waves as a function of:
   the set of insonification angles $\alpha_i$,
   a geometry of the curved array of virtual transducers which includes the reference center and the radius of curvature $r_n$, and
   the distance r from said at least one scatterer to the reference center, and wherein each local wavefront orientation satisfies the following formula:

$$\alpha_{eq,i} = \arcsin\left(\frac{r_n}{r}\sin\alpha_i\right).$$

2. The apparatus according to claim 1, wherein the driving and processing unit comprises a controller configured to drive the generator in order to generate at least two series of excitation signals at a constant repetition interval, and configured to drive the curved array of virtual transducers in order to transform said at least two series of excitation signals into Archimedean spiral waves, wherein:
a first series of excitation signals allows the obtaining of a first gathering of scattered signals, and
a second series of excitation signals allows the obtaining of a second gathering of scattered signals.

3. The apparatus according to claim 2, wherein the driving and processing unit comprises a beamformer which:
receives said first and second gatherings of scattered signals generated by scattering of said Archimedean spiral waves,
delays and sums said first gathering of scattered signals in order to generate first groups of receive beams having a respective receive angle, each group of receive beams corresponding to a respective insonification angle,
delays and sums said second gathering of scattered signals in order to generate second groups of receive beams having a respective receive angle, each group of receive beams corresponding to a respective insonification angle.

4. The apparatus according to claim 3, wherein each of the first and second groups of receive beams comprise a plurality of images, each image being associated with a respective pair of insonification angle and receive angle, and wherein the driving and processing unit further comprises a processor configured to Doppler process said first and second groups of receive beams for any given pair of images of the first and second groups of receive beams having the same pair of insonification angle and receive angle so that velocity fields are estimated for each pair of distinct spiral orientations and receive beam orientations.

5. The apparatus according to claim 4, wherein the processor is configured to implement the following steps for each pair of images of the first and second groups of receive beams having the same pair of insonification angle and receive angle:
estimating a displacement field for each corresponding pixel between the images of a given pair of images,
estimating, from the displacement field, a doppler frequency shift per pixel for said given pair of images.

6. The apparatus according to claim 4, wherein the processor is to implement an algebraic inversion step where several projections of the velocity field and their known orientations are used to estimate radial and azimuthal components of the velocity field.

7. The apparatus according to claim 6, wherein the processor is configured to estimate axial and lateral velocity components from the radial and azimuthal components of the velocity field.

8. A method for estimating the velocity of at least one scatterer in a medium, wherein the method comprises:
generating of excitation signals,
transforming of said excitation signals into Archimedean spiral waves,
emitting said Archimedean spiral waves in a plurality of predetermined directions of propagation defined by a set of insonification angles, a curvature of said curved array of virtual transducers defining a reference center and a radius of curvature,
receiving scattered signals generated by scattering of said Archimedean spiral waves emitted from said curved array of virtual transducers,
estimating the velocity of the at least one scatterer,
wherein axial and lateral velocity components are estimated using a set of local wavefront orientations $\alpha_{eq,i}$ of the Archimedean spiral waves as a function of:
the set of insonification angles $\alpha_i$,
a geometry of the curved array of virtual transducers which includes the reference center and the radius of curvature $r_n$, and
the distance r from said at least one scatterer to the reference center, and wherein each local wavefront orientation satisfies the following formula:

$$\alpha_{eq,i} = \arcsin\left(\frac{r_n}{r}\sin\alpha_i\right).$$

9. The method according to claim 8, wherein:
the step of generating excitation signals includes generating at least two series of excitation signals at a constant repetition interval, and
the step of transforming includes transforming said at least two series of excitation signals into Archimedean spiral waves:
a first series of excitation signals allowing the obtaining of a first gathering of scattered signals, and
a second series of excitation signals allowing the obtaining of a second gathering of scattered signals.

10. The method according to claim 9, wherein the step of estimating the velocity of the at least one scatterer includes a beamforming substep comprising:
receiving said first and second gatherings of scattered signals generated by scattering of said Archimedean spiral waves,
delaying and summing of said first gathering of scattered signals in order to generate first groups of receive beams having a respective receive angle, each group of receive beams corresponding to a respective insonification angle, and
delaying and summing of said second gathering of scattered signals in order to generate second groups of receive beams having a respective receive angle, each group of receive beams corresponding to a respective insonification angle.

11. The method according to claim 10, wherein each of the first and second groups of receive beams comprise a plurality of images, each image being associated with a respective pair of insonification angle and receive angle, the step of estimating the velocity of the at least one scatterer further comprising:
Doppler processing of said first and second groups of receive beams for any given pair of images of the first and second groups of receive beams having the same pair of insonification angle and receive angle so that velocity fields are estimated for each pair of distinct spiral orientations and receive beam orientations.

12. The method according to claim 10, wherein the step of estimating the velocity of the at least one scatterer further includes the following substeps for each pair of images of the first and second groups of receive beams having the same pair of insonification angle and receive angle:
estimating of a displacement field for each corresponding pixel between the images of a given pair of images,
estimating, from the displacement field, a doppler frequency shift per pixel for said given pair of images.

13. The method according to claim 10, wherein the step of estimating the velocity of the at least one scatterer further includes an algebraic inversion step where several projections of the velocity field and their known orientation are used to estimate radial and azimuthal components of the velocity field.

14. The method according 13, wherein the step of estimating the velocity of the at least one scatterer further includes computing the axial and lateral velocity components from the radial and azimuthal components of the velocity field.

* * * * *